(12) United States Patent
Siegel

(10) Patent No.: US 6,766,277 B2
(45) Date of Patent: Jul. 20, 2004

(54) EARLY WARNING NETWORK FOR BIOLOGICAL TERRORISM

(75) Inventor: Neil G. Siegel, Ranch Palos Verdes, CA (US)

(73) Assignee: Northrop Grumman Corporation, Los Angeles, CA (US)

( * ) Notice: Subject to any disclaimer, the term of this patent is extended or adjusted under 35 U.S.C. 154(b) by 75 days.

(21) Appl. No.: 09/882,886

(22) Filed: Jun. 15, 2001

(65) Prior Publication Data

US 2002/0193967 A1 Dec. 19, 2002

(51) Int. Cl.[7] .......................... G06F 15/00; G06F 17/60
(52) U.S. Cl. ............................. 702/187; 705/2; 705/3
(58) Field of Search ........................... 702/187; 705/1, 705/2, 3, 10, 14; 706/924

(56) References Cited

U.S. PATENT DOCUMENTS

| | | | | |
|---|---|---|---|---|
| 3,926,071 A | * | 12/1975 | Elliot | 235/104 |
| 5,911,132 A | * | 6/1999 | Sloane | 705/3 |
| 6,129,274 A | * | 10/2000 | Suzuki | 235/381 |
| 6,430,305 B1 | * | 8/2002 | Decker | 340/5.41 |
| 2001/0014868 A1 | * | 8/2001 | Herz et al. | 705/14 |
| 2002/0040365 A1 | * | 4/2002 | Price et al. | 707/100 |

OTHER PUBLICATIONS

National Center for Infectious Diseases—Infectious Disease Surveillance http://www.cdc.gov/ncidod/osr/site/surv_resources/surv_sys.htm.*

* cited by examiner

*Primary Examiner*—John Barlow
*Assistant Examiner*—Meagan Walling
(74) *Attorney, Agent, or Firm*—Ronald M. Goldman

(57) ABSTRACT

A computerized early warning network for biological events or terrorism produces the alert that calls the health authorities to action. Data generated in the point of sale (POS1 . . . POSn, POSa & POSb) units of a retail store or pharmacy that sells prescription and non-prescription medicines contain information regarding purchases of various medicines which are available at the central server (S2) associated with the point of sale equipment. The database of purchases is periodically culled to extract information regarding the quantities of different types of medicines purchased (PROG) in the period, such as over a day, and that information is transmitted, directly or indirectly, to the servers (S3) of the public health authorities. With medicine type correlated to specific diseases, the computers of the health authorities evaluate the purchase information on a type-by-type basis and region-by-region basis to determine occurrence of a biological event in any of the regions.

11 Claims, 3 Drawing Sheets

Database No. 1
| Item | | Quantity | Price Ea. | Total | Date | Time | Club Member No. | Cred. Card | Cust. Name | Store | Zip Code |
|---|---|---|---|---|---|---|---|---|---|---|---|
| Brand | Type | | | | | | | | | | |
| | | | | | | | | | Grand Total | | |
Figure 3
Selection Criteria
| Medication Type | Application |
|---|---|
| A | Colds, Headache |
| B | Flu |
| C | Diarrhea A |
| D | Lice |
| E | Pain Killer |
| ... | |
| N | Cholera |
Figure 4
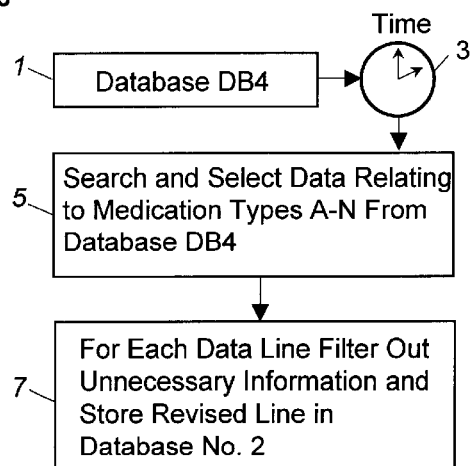
Figure 5
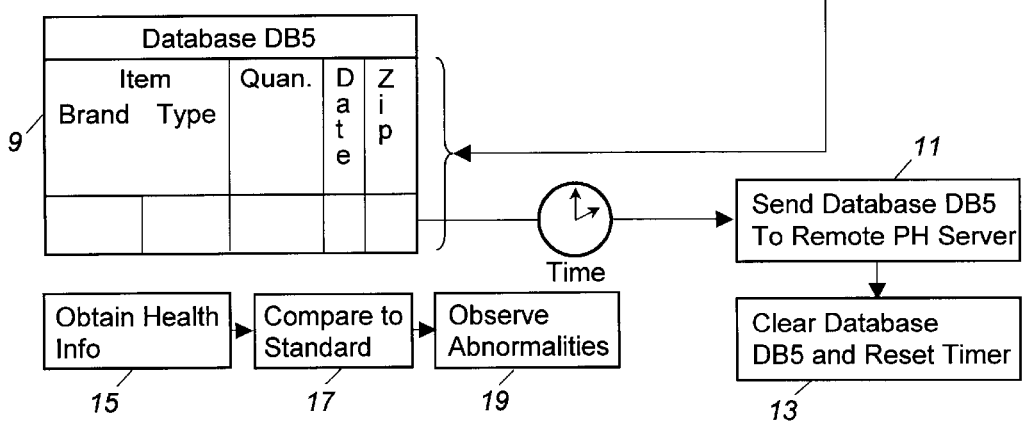
Figure 6

EARLY WARNING NETWORK FOR BIOLOGICAL TERRORISM

FIELD OF THE INVENTION

This invention relates to management information systems for monitoring the public health, and, more particularly, to a computerized system for collecting information relevant to the incidence and type of disease and other off-nominal medical conditions among the general population, and compiling and analyzing that information. The system alerts the public health authorities to the presence of particular diseases or other off-nominal medical conditions in defined geographical regions, including diseases or other off-nominal medical conditions that could result from an act of biological or chemical terrorism; and serves as an "early warning network" for events of biological causes.

BACKGROUND

Public health management information systems gather information on the incidence of disease, information that enables the health authorities to act and, ideally, block the outbreak of an epidemic of disease. As a public health measure, the various States of the United States currently require treating physicians to notify public health authorities of the discovery of certain contagious diseases in a patient. The physician may give that notice by telephone or facsimile. Through that notification procedure relevant data of disease is collected.

Although the purpose of that notification is commendable, the procedure takes time from the physician's very busy schedule (or that of the physician's staff). In recent years physicians (and the physician's staff) have become busier than ever, overloaded with patients and paperwork, which inhibits reporting. Even so, the foregoing manual reporting system works, particularly when the disease is recognized as being of a very serious nature. As example, as reported in the newspapers recently, when a female business traveler, who flew by airplane between an African country to Canada and to the U.S., fell ill and was thought to have contracted the deadly and highly contagious Ebola virus, the reporting was swift. The report was followed by quick action taken by the public health authorities.

In addition to the reports prepared by physicians, there are other potential sources of important information regarding public health that may be culled. Examples include statistical information regarding the purchase of over-the-counter medications, and statistical information regarding school absence rates and work absence rates. The collection and compilation of such statistical information very labor-intensive and not done systematically.

For the majority of diseases or other off-nominal medical conditions, however, the foregoing collection and/or reporting procedure is unreliable, uncertain, and slower than desired. The public health authorities might even wish that it were possible to learn of the incidence of a disease without troubling the attending physicians or their staff. As an advantage, the present invention accomplishes such a task. With the present invention, pertinent data are gathered from many sources, including those previously cited; and the invention provides rapid and reliable correlation of such multi-source data into a more timely and more reliable warning of biological incidents.

Typically a large time delay occurs between the occurrences of a biological event, such as caused an accidental spill, accidental contamination, or an act of biological terrorism, and the time at which the public health authorities are able to conclude that a biological event is underway. In part, the delay is due to the gestation period of the biological agents that were released by the event, but most of the delay is caused by failing to notice a pattern of events until the effects are quite pronounced. Typically, the delay is on the order of a few weeks. Given the propagation patterns of biological agents, shortening delays in detection would have a major benefit in containment, diagnosis, and treatment.

For example, assume that a water plant serving a particular community becomes contaminated. Such contamination might be caused by a contaminated filter or by a filter that is incorrectly prepared prior to being placed in service. Such contamination might also be deliberately caused by an act of terrorism. In either event, some time will lapse before anyone notices the contamination or the effect of the contamination. The incident is likely to be more severe if the time delay to detection is longer, and less severe if the time delay is shorter. Hence, approaches that shorten the time delay are highly advantageous.

One device that could give notice is the monitoring device for the water of the treatment plant. The existing state of the art for sensors that are able to detect biological agents, however, appears to be fairly primitive. Existing sensors tend to be expensive, slow, require large sample sizes, and have no effective "stand-off" range (e.g., they must be located in very close physical proximity to the event). For many threat scenarios, the more likely "first notice" is less direct: The symptom observed is that many people start to fall ill. It is recognized that at any given time and place, a large number of people fall ill for many reasons. But by noticing that an abnormal trend of illnesses is taking place, one is able to ultimately detect the foregoing contamination.

The foregoing example of water plant contamination is not theoretical. Not long ago the population of a large city in the northern U.S. suffered a large number of illnesses and even deaths due to what turned out to be a fault in a local water treatment facility. First it was noticed that many people inexplicably became seriously ill; some died. After a while it became apparent that rates for certain events were well above normal. Only many weeks thereafter was information correlated to the point where the authorities were able to form a hypothesis regarding the cause. And more time passed before the correct cause was found and corrected. From the perspective of public health, the incident would have unfolded exactly the same way if the cause of the incident were due to deliberate contamination of the water treatment plant, rather than poor maintenance (as turned out to be the case). In the foregoing, the effect described appeared well before the cause could be determined.

An after-the-fact analysis of the incident shows that the first potential indicator of a problem was a huge increase in the purchase of over-the-counter anti-diarrhea medications. This was followed (several days later) by an increase in doctor visits by patients with similar complaints. Even later, hospitalizations and deaths followed. The present inventors recognize that the affected population turned first to self-diagnosis and self-medication, and only sought professional advice several days thereafter. Thus, the first clue of the existence of a problem would have been indications of the increase in the purchase of over-the-counter medications. As an advantage, the present method looks to the latter purchase information automatically. With the method described herein the foregoing incident would have unfolded differently. Through automatic culling of the first indication information as offered by the present invention, the method would have led to diagnosis and correction of the problem several weeks earlier than actually occurred. Many illnesses could have been moderated or avoided, and many deaths perhaps could have been avoided.

The foregoing example originated in part due to the neglect of some person or other. Diseases may also be cultivated and broadcast by nations as a weapon of war for disabling an enemy, or even as a weapon of terrorism. Terrorism is a technique by which a militarily-impotent barbaric state may secretly wage war (or, following defeat, continue to wage war) against a more powerful but "civilized" opponent in the hope that the terrorist acts cripple and/or demoralize the civilized foe to the point where the civilized foe loses its "will", and is internally rendered defenseless. Because of the ability of a terrorist to hide their role if they elect to do so, the civilized state is without proof as to the source of the terror, and, typically, is therefore unable to take direct action against the perpetrator. Indeed, the perpetrator may not even be a nation-state, but may be individuals or private organizations.

One typically equates a terrorist act with bombs exploding for maximum effect in heavily populated locations. Despite the damage caused, the range of a bomb is limited. Nor does bomb damage continue to grow over time. However, a disease that is easily spread, such as by the wind, can cover much larger regions, causing greater numbers of innocents to become sickened and/or die. And, because biological agents are alive and can continue to grow and multiply, the damage can actually increase over time.

Biological terrorism is a present serious concern. Civilized nations remain apprehensive of the possibility of such a biological terrorist attack. In particular, with the existence of a predator in control of a nation creating weapons of mass destruction and secretly conducting a war of terrorism, nations are well advised to monitor for surreptitious biological attack. To do so in great part leads one back to the existing public health management information system earlier described, and the delays attendant therein.

A need therefore exists for a more effective means for early detection of the incidence of disease and other off-nominal medical conditions. As an advantage, the present invention provides early warning of a potential epidemic or biological attack, or at a minimum, places officials on notice of facts bearing further investigation. The invention is effective against deliberate events (e.g., biological terrorism), accidents causing release of biological agents (e.g., the defective filter in the water treatment plant, as in the above example), and natural biological events (e.g., epidemics).

Ideally, an effective monitoring system is one that is practical, inexpensive, easily replicated, and makes use of existing infrastructure to the greatest extent possible. The present invention fulfils each of those goals.

The present invention is based on observation of human nature. As applicants have observed, when feeling bad, people often self-diagnose their condition and attempt to self-medicate before resorting to a visit to a doctor. On a macro scale, the purchase of over-the-counter medicines provides the earliest clue. As example, increased sales of aspirin in a given locale may indicate the onset of the flu, some local event causing stress, or something else. Given the clue (e.g., sales of some over-the-counter medicine significantly higher than normal), health authorities may investigate in that locale for particulars. Additionally, if the symptoms of the illness do not lighten thereafter, but deepen, and the person feels seriously ill, then the person will visit the doctor. Typically, the doctor will issue a prescription for medicine, and the patient will purchase the medicine at a pharmacy. In each case, a record is typically made of the purchase transaction.

Most everyone has witnessed the technological changes introduced in recent time into the modern supermarket, drug stores, and other retail establishments that have dramatically altered the way retail business is done. Such innovations include the bar-code reader, the bar-coded labels on packaging, the cash register that reads the information scanned by the bar code reader, and the credit card reader that is also connected to the cash register, collectively referred to as point-of-sale ("POS") equipment. The use of POS equipment has greatly increased the efficiency and speed of the check-out procedure, and reduced errors in entering data at the cash register. It also provided the customer with greater information of the purchases that were made.

The receipt handed to the customer includes a print-out that details the identification of the items that were purchased, the individual product prices, the tax, if any, the total price, and even some promotional material or advertising. Often a coupon is printed out and handed to the customer along with the receipt. Typically the coupon is for a product that is of the same kind or competitive to a product that the customer has purchased. Such an action gives rise to another important aspect to the POS equipment that is generally transparent to the customer; the computer of the POS equipment collects and uses information gathered at the cash register, and stores that information in a peripheral memory of the computer, such as a disk drive.

For one, the computer can be programmed to save the information collected by ringing up purchases of an individual customer at the register, scan that information to detect the presence within the purchases of a kind of product whose sales are to be monitored, and, if so, command the print-out at the cash register of a particular coupon for the customer. The information collected from the cash register can be used for inventory control purposes within the store. As example, the initial store inventory is maintained in a database. Each item scanned in a sale may be subtracted from the count of the respective item in the database, lowering the amount in inventory. Store management can determine "what's hot, and what's not".

Further, when and if the inventory of a particular item is found to fall below the predetermined "reorder" level set by management for the item, a reorder alert may be printed out at the POS computer. If the particular store is part of a chain of stores, the sale and inventory information is often transmitted daily to headquarters of the chain. Headquarter management is then able to watch for aberrations in the business of any particular store and even "second guess" the manager of the local store. In essence, the database of the POS computer is a relative cornucopia of information.

One might not ordinarily think that the POS system of the drug store or supermarket could serve as a component of a public health management information system. The present applicant recognizes that large volumes of medicines, particularly over-the-counter medications, are sold directly to consumers to cure various ills; and that such sales are presently typically recorded in the database of POS equipment in the retail store. As becomes apparent, as a further advantage the present invention takes advantage of the widespread availability and capability of such POS equipment in the interest of public health and/or the national security. The invention borrows information gathered by existing POS equipment.

Accordingly, an object of the invention is detection of contagious diseases and other off-nominal medical conditions at the earliest opportunity.

Another object of the invention is to provide a method and system for detecting acts of biological terrorism in the general population. And A further object of the invention is to provide a cost effective disease detection system that is capable of accomplishment through existing technology.

SUMMARY

The present invention provides an early warning network that operates against a broad class of public health threats, such as bio-terrorism, accidental biological events, and/or naturally occurring diseases. By periodically extracting information from point-of-sale systems and similar information systems in retail businesses on purchases of medicine during a reporting period, and analyzing the acquired information, one may thereby detect an abnormal trend. Combining the purchase information with information from other sources, such as doctor and hospital reports, and the like, will enhance and speed detection of an abnormal trend.

In accordance with the foregoing objects and advantages, an early warning network for biological events or terrorism produces the alert that calls the health authorities to action. Data generated in the point of sale units of a retail store or pharmacy that sells prescription and non-prescription medicines contains information regarding purchases of various medicines which is available at the servers associated with the point of sale equipment. The databases of purchases are periodically culled to extract information regarding the quantities of different types of medicines purchased in the period, such as a day, and consolidated. The information is transmitted, directly or indirectly, to the servers of the public health authorities. With medicine type correlated to specific diseases, the computers of the health authorities evaluate purchase information on a type-by-type and region-by-region basis, allowing the authorities to identify trends and potential events far earlier than at present.

Protection of privacy and commercially-sensitive information is also a key advantage of the proposed system. The public health authorities (or whomever is operating the proposed system) do not need to "reach into" the computer systems of retail store chains in order for the proposed system to function. Instead, the public health authorities need only provide the store chains documentation defining the content and format of the data needed, and the desired frequency of reporting. The retail store chain can program their own computers to extract and formulate the needed information, and send the information to a designated recipient computer via the Internet or similar communication mechanism. The foregoing procedure protects the privacy of commercially sensitive information; the retail store chain need not allow outside organizations to "reach into" their computers in order to participate.

As an additional advantage, the system does not need information on a person-by-person basis; aggregated information that has no names or other specific individual identifiers attached is adequate for the purposes of the system. Thus the privacy of the individual consumers who purchase items at the retail store chains is protected. Retail store chains are able to properly advise their customers that no personal information is disclosed via the reporting process. The invention achieves a significant public benefit without any adverse impact on either commercial or consumer privacy.

The foregoing system permits national health authorities to be pro-active in ferreting out a potential epidemic or bio-terrorism event. When a trend is spotted that may indicate an unusual disease in a geographic region, the authorities may immediately contact the hospitals in the region to question unusual events. The authorities can even request samples for analysis from the hospitals for an independent assessment without requiring the identity of the patient.

The foregoing and additional objects and advantages of the invention, together with the structure characteristic thereof, where were only briefly summarized in the foregoing passages, will become more apparent to those skilled in the art upon reading the detailed description of a preferred embodiment of the invention, which follows in this specification, taken together with the illustrations thereof presented in the accompanying drawings.

BRIEF DESCRIPTION OF THE DRAWINGS

In the drawings:

FIG. 3 is a chart of a typical format of information recorded in a point of sale equipment;

FIG. 4 is a chart correlating particular types of medicines and the biological problem that the respective medicine alleviates or cures;

FIG. 5 illustrates the algorithm of the software program used in the point of sale computer in the system of FIG. 1 to format and send the information to the health authorities;

FIG. 6 illustrates the procedure for evaluating the received information to detect abnormal incidence of disease;

DETAILED DESCRIPTION OF THE PREFERRED EMBODIMENTS

Figure 1:
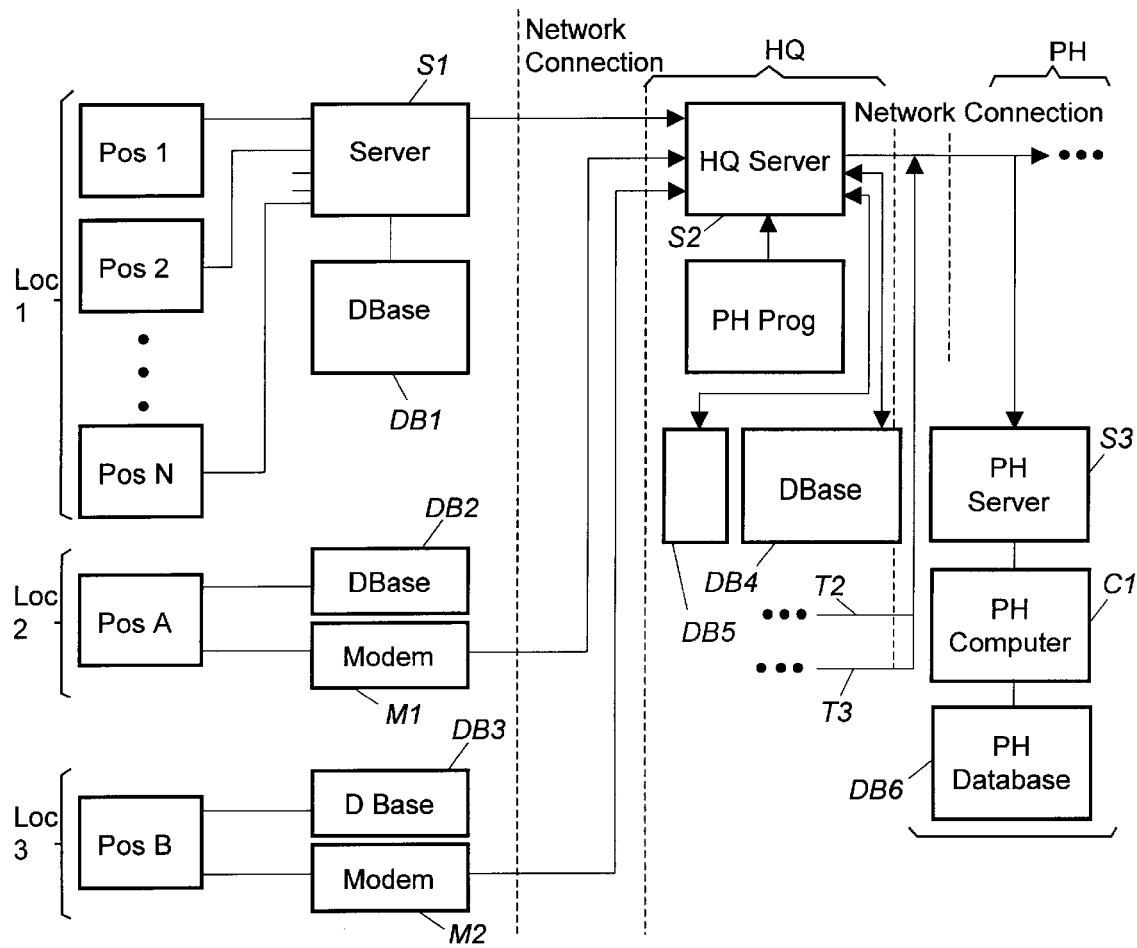
FIG. 1 illustrates an embodiment of an early warning system in accordance with the invention.

Reference is made to FIG. 1, which illustrates an embodiment of the novel early warning network. Many retailers in a geographic region typically sell medicine; and each of those retail establishments possesses and uses point of sale equipment, the structure, content and operation of which is well known to those in the business. A large retail store typically contains many POS stations that are hard-wired to a server located in the store. The individual point of sale equipment of that retailer is represented in FIG. 1 as LOC 1 and the respective blocks POS 1 through POS n, where n may be any number that represents individual POS stations in the store. Each station is connected via a network cable to the in-store server S1. The store's database of sales information is maintained in database DB1.

A network connection permits server S1 to communicate with a server S2, the "HQ Server", maintained by the management of the store typically found at a headquarters location remote from the large store. There may be multiple such headquarters servers, arranged in a hierarchy. The network connection may be made via the telephone network and the Internet, may be a direct telephone connection, or may be a wireless connection. At present, the use of the telephone network and Internet is common. Typically, server S1 will have a dedicated telephone connection to the Internet by means of a cable modem, ISDN, DSL, and/or the like. Communication between servers S1 and S2 may be initiated, as desired, by server S2 functioning to poll server S1 on a daily basis for the sales information for the day. Alternatively, server S1 may initiate the communication at a certain time of day by automatically logging on to server S2. As becomes apparent, the particular technique employed does not have a significant affect upon the operation of the proposed invention.

A small size retail store, such as represented as LOC 2, typically does not include a server. The POS equipment, POS A, in the store, typically contains a database, DB2, for sales information collected at the store and a modem, M1 to enable the POS of the store to connect via a dial-up modem connection over the Internet to the server of the store's management. In the illustrated system, the small store is presumed to have the same management as the store at LOC 1, and, hence, the station connects via the telephone network to server S2.

Another small size store is illustrated at LOC 3 and reports to the same management location at server S2. This location includes the POS B, a database DB3 and a modem M2. As one appreciates the foregoing is intended to be for purposes of illustration. A retail chain may contain many more large stores and, perhaps, many more small stores than that illustrated in FIG. 1, all of which may communicate with the headquarters server, using a variety of methods and topologies.

At the headquarters location, server S2 is associated with a database, DB 4 and with another database DB5, the latter of which is dedicated to the health monitoring system. The server contains various programming, including the program for the health reporting system, PH PROG, later herein more fully described. Apart from the program PH PROG, the foregoing components are intended to illustrate known POS equipment and their networking relationship.

The station or stations of the public heath ("PH") authorities includes a server S3, a programmed computer C1, and the database DB6 for storing information. The public health server S3 connects to the same network as the HQ server S2, which for purposes of this illustration is the public telephone network and the Internet. It should be appreciated that servers that are associated with other retail stores or retail chain headquarters, different from server S2, will also network to the public health server S3. Lines T2 and T3 in the figure symbolically illustrate the connection for those other stores to the telephone network. As those skilled in the art recognize the foregoing connections may be accomplished by a variety of methods and topologies; and that the invention is not limited to the specific means of the embodiment.

Each stand alone POS station, such as POS A and POS B, and each server, such as S1, of a group of POS stations, POS1–POSn, contains a database of customer product purchase information, such as described in the background section of this application. Each contains some means to communicate that sales information to a central location, such as server S2, in the normal operation of the information management system of the retail store or retail chain.

Figure 2:
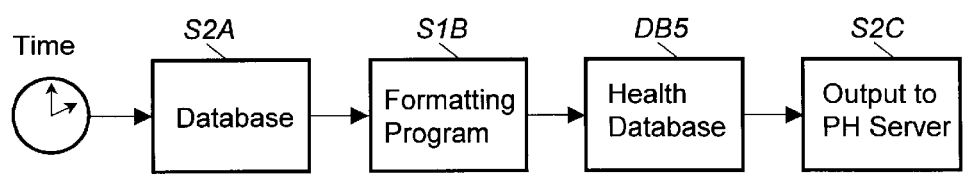
FIG. 2 is a functional block diagram of the headquarters server for the POS equipment as used in the embodiment of FIG. 1.

FIG. 2 is a block diagram of a server, showing the flow of data in the headquarter server S2 of the large store as adapted to the present system. The server includes a programmed computer programmed to carry out the normal functions for the POS operations and a POS database, typically stored in a hard drive controlled by the computer. The computer also includes the acquisition program that adapts the headquarter server of the POS system to the present monitoring system. The health system acquisition program retrieves selected data from the POS database S2A, formats the data S2B to the format required by the health system and stores than information, at least temporarily, in the Health database DB5. At the appropriate time the stored formatted data is output S2C from the server S2 of the store for transmission to the server S3 of the health system, shown on the right. The requirements of the adaptation program are discussed in greater detail later herein in connection with the succeeding figures of the drawings.

FIG. 3 is a chart of data as may be currently maintained in the database of the point of sale equipment for normal retail. The data may be formatted (that is, ordered) in the order illustrated, and may include the specific items indicated: Product Brand, Product type, quantity, unit price, total, date, time, club member number, credit card number, customer name, store number, and store zip code. Not all of the foregoing information may be available for a particular purchase, as example, if the customer does not use a credit card to make the purchase. Thus the purchase of many different commodities or products will produce a corresponding number of lines of the formatted data. When the purchase is completed, the computer adds all of the totals to obtain a grand total, and prints out that information on the cash register receipt. The foregoing data are preserved, at least for the day, and may be compiled to achieve the inventory control and other information earlier described.

FIG. 4 is a chart that correlates the type of medicinal product with a possible ailment. Although the information obtained by the POS equipment may include product type, it may be rare for that equipment to be programmed to associate the medicinal type with specific ailments and/or conditions. The chart is useful in programming for the computer C1 (FIG. 1) of the health authorities. When the data for type is received and printed out or otherwise displayed to the operator of the Health computer C1, the various ailments associated with the medicines will be displayed to the system operator in a visually perceptible and recognizable manner. The relationship between the two columns of FIG. 4 may be one-to-N, that is, each medicine may be associated with multiple ailments and/or conditions. For example, aspirin is used both to treat pain and to lower fever.

FIG. 5 illustrates the process carried out by the program installed in the computers of the diverse POS systems. During the day the POS computer accumulates the data of all purchases made by the retail customers in the associated database DB4, represented by block 1. That data is formatted, as example, as presented in the chart of FIG. 3 and is available in the database. At the end of each day (or other selected interval of time as the designer may specify), as represented by the clock symbol 3, the program that selects and formats data for the public health server is started. As represented by block 5, the acquisition program searches through the database DB4 for purchase information on the types of medication products, such as found in the chart of FIG. 4. The program selects the data items by the desired criteria, and may store the retrieved data items in temporary memory. Then, as represented at 7, for each line of such data that was retrieved, the program filters out extraneous information, leaving only the relevant information being sought. As example, the acquisition program retrieves only the type, quantity, date information and zip code from each line of selected data and stores that information in a second database, represented by Database DB5, block 9 in the figure. As is recognized, both databases DB4 and DB5 may occupy separate portions of the same disc drive, or may be on separate disk drives.

When completed, the program may then total the quantities for each type of medicine. Alternatively, the program may maintain a simplified database containing only the various types of medicines, the quantity and the date; and establish a running count for each medicine. That is, when the program retrieves data for a purchase of Medication type A, as example, the program first checks the date in the line of data and compares that to the date of the database. If the same, the quantity found in the quantity column of the line of data is added to the quantity column in database no. 2 and the new sum is then stored in the quantity column of the database. In the foregoing manner, a running count may be established for each pertinent type of medicine. With either approach, the total of each type of medicine is obtained for the prescribed period. Once the program determines that each line of data for the time period has been polled, the program saves the running totals and initiates transmission of that information to the public health server S3, as represented by block 11.

Returning to FIG. 1, the acquisition program automatically initiates a connection via server S2 over the internet (or other network if used) to access the public health server S3, entering the appropriate access code, if an access code is required. Once code confirmation is accepted, the program in server S2 transmits the data from Database No. 2 to the public health server S3, which downloads the information into the public health computer C1 and thereby into the public health database DB 6.

Returning to FIG. 5, by signaling completion and verification of transmission, the acquisition program then terminates the networking and disconnects, clears database DB5 and then resets, represented by block 13 awaiting the repeat of the operation that occurs the same time on the following day (or other selected interval or period).

Referring again to FIG. 1, following download of the information from various retail sources to health system server S3, as example, the next morning, the health data in the health database DB5 are then analyzed and evaluated. As illustrated in FIG. 6, the health data are retrieved by the health system computer as represented at 15, and that information is compared on a medicine-type-by-medicine-type basis, and by region, for example, by zip code or groups of zip code, as represented at block 17, and the changes or abnormalities, if any, from a prescribed standard observed, as represented at block 19. As is typical the health system computer system includes a computer monitor or other display apparatus, not illustrated. The changes or abnormalities may be displayed as a text or graphic file on the monitor, and allow the data to be displayed in different ways, as example, abnormalities nationwide (e.g., all zip codes), or on a geographically-distributed basis. Alternatively, the display may contain a map of the U.S. and the abnormalities uncovered may be overlain on the map at the particular geographic location. Many other alternatives (e.g., audio and visual alarms) are apparent to those skilled in the display art.

As an advantage the foregoing system is essentially self-calibrating. Any system that depends on the detection of off-normal data, such as described in the preceding text, requires knowledge of normal data, a "baseline" against which to calibrate and define a range of nominal values. Often that information is difficult, expensive and/or impractical. An important feature of the present invention is the ability to gather such base-lining and calibration data automatically. By operating the described system for some period of time under normal circumstances the data acquired for the respective intervals is representative of what is normal, which presumes there is no significant unusual biological outbreak during the period. The information may then be saved and used thereafter as the standard against which comparisons are made.

Figure 7:
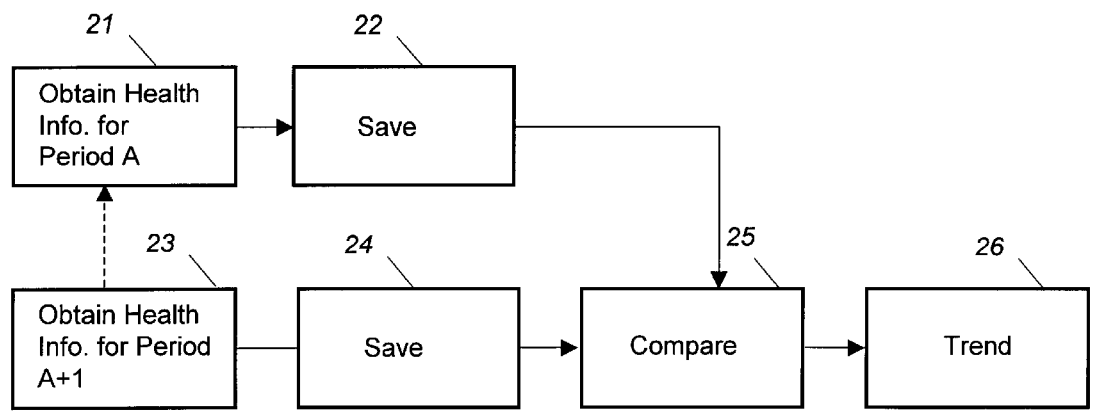
FIG. 7 illustrates a modification of the evaluation procedure of FIG. 6 to enable detection of trends.

The data received at the health system server S3 may also be used to detect a trend. As illustrated in FIG. 7, the health information obtained for one period A, represented at 21, such as one day, during a check at a predetermined hour at the end of the day may be stored 22. When the next checking interval occurs twenty-four hours later, the corresponding health information for the period A+1, represented at 23, is obtained and stored 24. The latest information may then be compared 25 with the earlier acquired health information to provide the changes, as may show a trend 26. Thereafter, the later acquired information replaces the earlier acquired information, allowing the trend spotting procedure to repeat with later information acquired at the next check.

Figure 8:
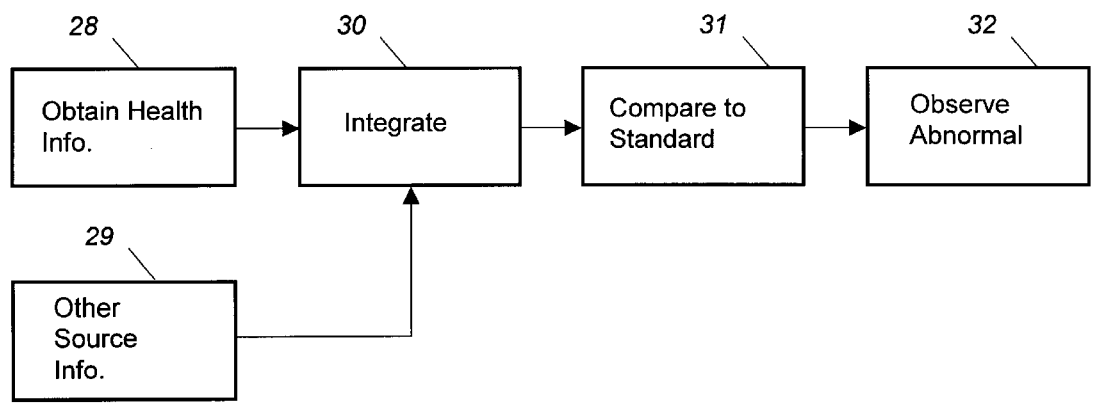
FIG. 8 illustrates a further modification of the evaluation procedure of FIG. 6 in which additional information sources may be integrated within the analysis.

As a further refinement the health monitoring system may be modified to supplement the health data information obtained from the POS equipment with health information obtained from other sources, such as reports from hospitals and doctors, which is illustrated in FIG. 8. The health data information obtained from the POS equipment is represented as block 28. That information obtained from other sources of information is represented by block 29. Both groups of information are integrated as represented by block 30. The combined health data may then be compared to a standard, block 31, and any abnormalities observed, block 32. Even though information from other sources may be obtained less frequently than that from the POS equipment the additional information can only be helpful.

The foregoing system respects the privacy of individuals. No other computers "reach" into a source computer. Only the owner of the source computer determines what data are provided to the early warning network computers, and how often the data are supplied. The data are aggregated or compiled at a level that prevents disclosure of private information regarding the customers of the business. No names, addresses, phone numbers, social security numbers, credit card numbers, or any other identification of an individual is provided. No such information is requested.

A further advantage is that the invention is constructed using existing technology, and in great part, makes use of equipment that is already in place and in operation for other purposes, such as the point-of-sale equipment. All that is necessary to adapt such equipments to the present system is to incorporate a software program, and install that program in the POS or headquarters computers.

The existing state of the art for sensors that are able to detect biological agents appears to be fairly primitive. Existing sensors tend to be expensive, slow, require large sample sizes, and have no effective "stand-off" range. If and when such sensors are improved to the point where the production and maintenance cost is lowered significantly and the sample size requirement decreases significantly, then it will become practical to employ standing deployment of multiple sensors at key locations, such as at water processing systems, or to deploy a standing set of such sensors that are maintained ready but remain inactive until an alert signal is received. Any of such sensors may in the future be readily integrated within the architecture of the present system. Including data transmission components within the sensor system would allow the sensor to connect to or gain access to the central computer of the monitoring system, and send the information acquired daily/periodically into that computer. That information may be analyzed along with the public health information supplied by the retail establishments.

Considering the large number of retail establishments in the country that both possess point of sale equipment and sell medicine, it may be impractical to have all stations report at or after the end of the business day to a single location. Such an approach might overload the network, the web-site and/or result in busy signals. As those skilled in the computer communications art will appreciate, it is possible to arrange the system so that predefined groups of retail establishments access a respective one of a number of "central stations". Thereafter each of those central stations would automatically access and communicate the stored information to a super central station. Effectively instead of a parallel network arrangement, the latter arrangement forms an inverted pyramid network.

The foregoing method has been described as being operated by public health authorities. It should be understood that the system is not limited to use by any particular organization, private or government, and may be established and used by others as well. As one appreciates the public health services may take responsibility for operation of such a system and also may delegate operation of that service to a private party or organization under contract. Or the system could be undertaken and be used by a private concern that is interested in the subject.

It is believed that the foregoing description of the preferred embodiments of the invention is sufficient in detail to enable one skilled in the art to make and use the invention without undue experimentation. However, it is expressly understood that the detail of the preferred embodiment that was presented for the foregoing purpose is not intended to limit the scope of the invention in any way, in as much as equivalents thereto and other modifications thereof, all of which come within the scope of the invention, become apparent to those skilled in the art upon reading this specification. Thus, the invention is to be broadly construed within the full scope of the appended claims.

What is claimed is:

1. A computer assisted method of detecting arrival of a particular disease or biological event amongst a general population within a geographical region, comprising the steps of:
   monitoring of records maintained in point-of-sale equipment of purchases of medicine made by the general population within a prescribed period of time to obtain medicine purchase information; and
   analyzing the forgoing medicine purchase information to determine if a particular ailment is occurring with a greater than normal incidence for the period of time.

2. The computer assisted method of detecting arrival of a particular disease or biological event amongst a general population in a geographical region as defined in claim 1, wherein said step of monitoring purchases of medicine further comprises: checking at predefined intervals the purchases made during a prescribed interval of time to provide purchase data of medicine for successive time intervals.

3. The computer assisted method of detecting arrival of a particular disease or biological event amongst a general population in a geographical region as defined in claim 2, wherein said prescribed interval of time comprises twenty-four hours; and wherein the periodicity of said step of periodically checking comprises one check in each twenty-four hour period.

4. The computer assisted method of claim 1 wherein said step of analyzing said purchases further comprises the steps of:
   comparing a quantity of purchases far each particular type of medicine in said prescribed period of time to a predetermined standard for purchases of medicine of the particular type, and determining which types of medicine have increased in sales.

5. The computer assisted method of claim 4, wherein said predetermined standard for purchases of medicine of a particular type comprises the purchases for the immediately preceding period, wherein the rate of change of purchases may be determined to define a trend.

6. The computer assisted method of detecting the arrival of a particular disease or biological event amongst the general population within a geographical region, comprising the steps of:
   checking purchases of medicine made by the general population within a prescribed intervals of time during a calendar year, periodically, at predefined intervals to obtain medicine purchase information for medicine purchases made by said general population in successive intervals of time; and
   analyzing the medicine purchase information of medicine purchases made by said general population in a particular interval of time during the calendar year to determine if a part particular ailment is occurring with a greater than normal incidence for the particular interval of time in the calendar year.

7. The computer assisted method of claim 6, wherein said step of checking purchases of medicine further comprises the steps of:
   procuring purchase data for medicine from point of sale equipment, said point of sale equipment being distributed about a geographic region, and storing said purchase data; and
   wherein said step of analyzing said purchases further comprises the steps of:
      comparing a quantity of purchases for each particular type of medicine in said prescribe period of time to a predetermined standard for purchases of medicine of the particular type, and determining which types of medicine have increased in sales.

8. The computer assisted method of detecting the arrival of a particular disease or biological event amongst the general population within a geographical region as defined in claim 6, which further comprises:
   checking other sources of data on illnesses currently being experienced in the general population during said predefined intervals; and wherein said step of analyzing the medicine purchase information of medicine purchase made in a particular interval of time includes the step of integrating the foregoing data on illnesses obtained from said step of checking other sources of data on illnesses.

9. A computer program for a point of sale apparatus of a retail store, said point of sale apparatus including: a computer, a network link to a remote computer to enable computer to computer communication, a networking program for accessing said remote computer, a database listing of products that were purchased by consumers during the course of a day, each said product listing including detail information of the type of said product and identification; said program for performing the steps of:

culling said database listing for medicine;

sorting each medicine culled from said database listing by ailments to which said medicine is known to be applied to provide a plurality of ailment groupings;

counting a number of purchases of medicine applicable to each of said plurality of ailment groupings to provide a plurality of counts;

initiating operation of said networking program to establish a network link to a predetermined remote computer;

sending the count for each of said plurality of groups to said predetermined computer when said network link is established; and terminating said network link to said predetermined remote computer following the sending of said count for each of said plurality of groups.

10. The computer program as defined in claim 9, wherein each said product listing also includes a zip code of the store at which the respective purchase of medicine was obtained; and wherein said step of sorting each medicine also includes sorting by said zip code.

11. The computer program as defined in claim 9, wherein said step of initiating operation of said networking program too establish a network link to a predetermined remote computer, comprises monitoring the time of day, and initiating operation of said networking program to automatically establish said network link when said time of day attains a predetermined time.

* * * * *